US011311295B2

(12) United States Patent
Wingardner et al.

(10) Patent No.: US 11,311,295 B2
(45) Date of Patent: Apr. 26, 2022

(54) ADAPTIVE POWERED STAPLING ALGORITHM WITH CALIBRATION FACTOR

(71) Applicant: Covidien LP, Mansfield, MA (US)

(72) Inventors: Thomas Wingardner, North Haven, CT (US); Elizabeth Contini, Trumbull, CT (US); Kelly Valentine, New Britain, CT (US)

(73) Assignee: Covidien LP, Mansfield, MA (US)

( * ) Notice: Subject to any disclaimer, the term of this patent is extended or adjusted under 35 U.S.C. 154(b) by 238 days.

(21) Appl. No.: 15/952,987

(22) Filed: Apr. 13, 2018

(65) Prior Publication Data
US 2018/0325517 A1  Nov. 15, 2018

Related U.S. Application Data

(60) Provisional application No. 62/506,180, filed on May 15, 2017.

(51) Int. Cl.
*A61B 17/072* (2006.01)
*A61B 17/115* (2006.01)
(Continued)

(52) U.S. Cl.
CPC .... *A61B 17/07207* (2013.01); *A61B 17/1155* (2013.01); *A61B 90/98* (2016.02);
(Continued)

(58) Field of Classification Search
CPC .......... A61B 2090/064; A61B 17/1155; A61B 17/07207; A61B 2017/00017;
(Continued)

(56) References Cited

U.S. PATENT DOCUMENTS 37,165 A    12/1862  Gary
2,245,994 A  6/1941  McWane
(Continued)

FOREIGN PATENT DOCUMENTS

AU   2008229795 A1   4/2009
CA    2451558 A1    1/2003
(Continued)

OTHER PUBLICATIONS

Extended European Search Report corresponding to EP No. 12 18 6177.7, completed Aug. 14, 2013 and dated Aug. 23, 2013; (8 pp).
(Continued)

*Primary Examiner* — Robert F Long
*Assistant Examiner* — Xavier A Madison
(74) *Attorney, Agent, or Firm* — Carter, DeLuca & Farrell LLP

(57) ABSTRACT

A surgical system includes: an adapter assembly; an end effector configured to couple to a distal portion of the adapter assembly; and a surgical device configured to couple to a proximal portion of the adapter assembly. The surgical device includes: a power source; a motor coupled to the power source, the motor configured to actuate at least one of the adapter assembly or the end effector; and a controller operatively coupled to the motor and configured to calibrate the motor while at least one of the adapter assembly or the end effector is actuated by the motor.

18 Claims, 9 Drawing Sheets

(51) Int. Cl.
  *A61B 17/00* (2006.01)
  *A61B 17/29* (2006.01)
  *A61B 90/98* (2016.01)
  *A61B 90/00* (2016.01)

(52) U.S. Cl.
  CPC .............. *A61B 2017/00017* (2013.01); *A61B 2017/00022* (2013.01); *A61B 2017/00039* (2013.01); *A61B 2017/0046* (2013.01); *A61B 2017/00057* (2013.01); *A61B 2017/00084* (2013.01); *A61B 2017/00398* (2013.01); *A61B 2017/00464* (2013.01); *A61B 2017/00473* (2013.01); *A61B 2017/00477* (2013.01); *A61B 2017/00725* (2013.01); *A61B 2017/00734* (2013.01); *A61B 2017/00738* (2013.01); *A61B 2017/07257* (2013.01); *A61B 2017/2904* (2013.01); *A61B 2017/2927* (2013.01); *A61B 2090/064* (2016.02)

(58) Field of Classification Search
  CPC .. A61B 2017/00022; A61B 2017/0039; A61B 2017/00398; A61B 2017/0046; A61B 2017/00477; A61B 2017/00725; A61B 2017/07257
  USPC ............................................ 227/175.1–182.1
  See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,079,606 A | 3/1963 | Bobrov et al. |
| 3,111,328 A | 11/1963 | Rito et al. |
| 3,209,754 A | 10/1965 | Brown |
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,695,058 A | 10/1972 | Keith, Jr. |
| 3,734,515 A | 5/1973 | Dudek |
| 3,744,495 A | 7/1973 | Johnson |
| 3,759,336 A | 9/1973 | Marcovitz et al. |
| 3,862,631 A | 1/1975 | Austin |
| 3,949,924 A | 4/1976 | Green |
| 4,060,089 A | 11/1977 | Noiles |
| 4,162,399 A | 7/1979 | Hudson |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,422 S | 10/1986 | Dickerson |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,722,685 A | 2/1988 | de Estrada et al. |
| 4,724,839 A | 2/1988 | Bedi et al. |
| 4,805,617 A | 2/1989 | Bedi et al. |
| 4,807,628 A | 2/1989 | Peters et al. |
| 4,823,807 A | 4/1989 | Russell et al. |
| 4,852,558 A | 8/1989 | Outerbridge |
| 4,874,181 A | 10/1989 | Hsu |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,118 A | 7/1992 | Walmesley |
| 5,129,570 A | 7/1992 | Schulze et al. |
| 5,143,453 A | 9/1992 | Weynant nee Girones |
| 5,152,744 A | 10/1992 | Krause et al. |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,301,061 A | 4/1994 | Nakada et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,427,087 A | 6/1995 | Ito et al. |
| 5,431,323 A | 7/1995 | Smith et al. |
| 5,464,144 A | 11/1995 | Guy et al. |
| 5,467,911 A | 11/1995 | Tsuruta et al. |
| 5,476,379 A | 12/1995 | Disel |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |

(56) References Cited

U.S. PATENT DOCUMENTS

| | | |
|---|---|---|
| 5,527,235 A | 6/1996 | Kuroda et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,558,671 A | 9/1996 | Yates |
| 5,560,532 A | 10/1996 | DeFonzo et al. |
| 5,562,239 A | 10/1996 | Boiarski et al. |
| 5,564,615 A | 10/1996 | Bishop et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,432 A | 5/1997 | Schulze et al. |
| 5,632,433 A | 5/1997 | Grant et al. |
| 5,634,926 A | 6/1997 | Jobe |
| 5,642,848 A | 7/1997 | Ludwig et al. |
| 5,647,526 A | 7/1997 | Green et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,692,668 A | 12/1997 | Schulze et al. |
| 5,693,042 A | 12/1997 | Boiarski et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,785,713 A | 7/1998 | Jobe |
| 5,788,698 A | 8/1998 | Savornin |
| 5,797,536 A | 8/1998 | Smith et al. |
| 5,810,811 A | 9/1998 | Fates et al. |
| 5,820,009 A | 10/1998 | Melling et al. |
| 5,823,066 A | 10/1998 | Huitema et al. |
| 5,829,662 A | 11/1998 | Mien et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,863,159 A | 1/1999 | Lasko |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,908,427 A | 6/1999 | McKean et al. |
| 5,911,121 A | 6/1999 | Andrews |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,159 A | 9/1999 | Nakamura |
| 5,954,259 A | 9/1999 | Viola et al. |
| 5,961,521 A | 10/1999 | Roger |
| 5,964,394 A | 10/1999 | Robertson |
| 5,964,774 A | 10/1999 | McKean et al. |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,993,454 A | 11/1999 | Longo |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,045,560 A | 4/2000 | McKean et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| 6,126,058 A | 10/2000 | Adams et al. |
| 6,126,651 A | 10/2000 | Mayer |
| 6,127,811 A | 10/2000 | Shenoy et al. |
| 6,129,547 A | 10/2000 | Cise et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,239,732 B1 | 5/2001 | Cusey |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |

(56) References Cited

U.S. PATENT DOCUMENTS

| | | |
|---|---|---|
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,330,965 B1 | 12/2001 | Milliman et al. |
| 6,343,731 B1 | 2/2002 | Adams et al. |
| 6,346,104 B2 | 2/2002 | Daly et al. |
| 6,348,061 B1 | 2/2002 | Whitman |
| 6,355,066 B1 | 3/2002 | Kim |
| 6,364,884 B1 | 4/2002 | Bowman et al. |
| 6,368,324 B1 | 4/2002 | Dinger et al. |
| 6,371,909 B1 | 4/2002 | Hoeg et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| 6,412,279 B1 | 7/2002 | Coleman et al. |
| 6,425,903 B1 | 7/2002 | Voegele |
| 6,434,507 B1 | 8/2002 | Clayton et al. |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,488,197 B1 | 12/2002 | Whitman |
| 6,491,201 B1 | 12/2002 | Whitman |
| 6,497,707 B1 | 12/2002 | Bowman et al. |
| 6,505,768 B2 | 1/2003 | Whitman |
| 6,515,273 B2 | 2/2003 | Al-Ali |
| 6,517,565 B1 | 2/2003 | Whitman et al. |
| 6,524,316 B1 | 2/2003 | Nicholson et al. |
| 6,533,157 B1 | 3/2003 | Whitman |
| 6,537,280 B2 | 3/2003 | Dinger et al. |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,610,066 B2 | 8/2003 | Dinger et al. |
| 6,611,793 B1 | 8/2003 | Burnside et al. |
| 6,616,821 B2 | 9/2003 | Broadley et al. |
| 6,629,986 B1 | 10/2003 | Ross et al. |
| 6,645,218 B1 | 11/2003 | Cassidy et al. |
| 6,651,669 B1 | 11/2003 | Burnside |
| 6,654,999 B2 | 12/2003 | Stoddard et al. |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,091,683 B1 | 8/2006 | Smith et al. |
| 7,097,089 B2 | 8/2006 | Marczyk |
| 7,097,858 B2 | 8/2006 | Hill et al. |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,225,964 B2 | 6/2007 | Mastri et al. |
| 7,238,021 B1 | 7/2007 | Johnson |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |

(56) References Cited

U.S. PATENT DOCUMENTS

| | | |
|---|---|---|
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Fates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0025891 A1 | 2/2002 | Colosky et al. |
| 2002/0049454 A1 | 4/2002 | Whitman et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0038938 A1 | 2/2003 | Jung et al. |
| 2003/0073981 A1 | 4/2003 | Whitman et al. |
| 2003/0114851 A1 | 6/2003 | Truckai et al. |
| 2003/0120306 A1 | 6/2003 | Burbank et al. |
| 2003/0139746 A1 | 7/2003 | Groiso |
| 2003/0165794 A1 | 9/2003 | Matoba |
| 2004/0094597 A1 | 5/2004 | Whitman et al. |
| 2004/0111012 A1 | 6/2004 | Whitman |
| 2004/0193146 A1 | 9/2004 | Lee et al. |
| 2004/0232199 A1 | 11/2004 | Shelton et al. |
| 2004/0232201 A1 | 11/2004 | Wenchell et al. |
| 2005/0000867 A1 | 1/2005 | Haynes et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006434 A1 | 1/2005 | Wales et al. |
| 2005/0010235 A1 | 1/2005 | VanDusseldorp |
| 2005/0023324 A1 | 2/2005 | Doll et al. |
| 2005/0067458 A1 | 3/2005 | Swayze et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0131442 A1 | 6/2005 | Yachia et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0178813 A1 | 8/2005 | Swayze et al. |
| 2005/0187576 A1 | 8/2005 | Whitman et al. |
| 2005/0192609 A1 | 9/2005 | Whitman et al. |
| 2005/0228341 A1 | 10/2005 | Edgerley |
| 2005/0247753 A1 | 11/2005 | Kelly et al. |
| 2006/0022014 A1 | 2/2006 | Shelton et al. |
| 2006/0022015 A1 | 2/2006 | Shelton et al. |
| 2006/0074405 A1* | 4/2006 | Malackowski ........ A61B 17/14 606/1 |
| 2006/0097025 A1 | 5/2006 | Milliman et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0151567 A1 | 7/2006 | Roy |
| 2006/0175375 A1 | 8/2006 | Shelton et al. |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0049435 A1 | 3/2007 | Jinno et al. |
| 2007/0055219 A1 | 3/2007 | Whitman et al. |
| 2007/0084896 A1 | 4/2007 | Doll et al. |

(56) References Cited

U.S. PATENT DOCUMENTS

| | | |
|---|---|---|
| 2007/0084897 A1 | 4/2007 | Shelton et al. |
| 2007/0101474 A1 | 5/2007 | Skottheim et al. |
| 2007/0101475 A1 | 5/2007 | Skottheim |
| 2007/0102472 A1 | 5/2007 | Shelton |
| 2007/0102473 A1 | 5/2007 | Shelton et al. |
| 2007/0125826 A1 | 6/2007 | Shelton |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175962 A1 | 8/2007 | Shelton et al. |
| 2007/0175964 A1 | 8/2007 | Shelton et al. |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0058801 A1 | 3/2008 | Taylor et al. |
| 2008/0109012 A1 | 5/2008 | Falco et al. |
| 2008/0110957 A1 | 5/2008 | McBride et al. |
| 2008/0110958 A1 | 5/2008 | McKenna et al. |
| 2008/0135600 A1 | 6/2008 | Hiranuma et al. |
| 2008/0164296 A1 | 7/2008 | Shelton et al. |
| 2008/0167670 A1 | 7/2008 | Shelton et al. |
| 2008/0167736 A1 | 7/2008 | Swayze et al. |
| 2008/0169329 A1 | 7/2008 | Shelton et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0185419 A1 | 7/2009 | Seong et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1* | 8/2010 | Ross .................... A61B 17/068 606/1 |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0290855 A1 | 12/2011 | Moore et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1* | 1/2014 | Snow ............. A61B 17/320016 606/130 |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0200851 A1* | 7/2014 | Weir .................. H02K 11/0094 702/182 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0209035 A1* | 7/2015 | Zemlok ................ G01D 18/008 73/1.01 |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |

(56) References Cited

U.S. PATENT DOCUMENTS

| | | |
|---|---|---|
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0100829 A1 | 4/2016 | Modesitt et al. |
| 2016/0100839 A1* | 4/2016 | Marczyk ......... A61B 17/07207 227/175.3 |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2017/0202607 A1* | 7/2017 | Shelton, IV ............ H02J 50/10 |

FOREIGN PATENT DOCUMENTS

| | | | |
|---|---|---|---|
| CN | 101234033 A | 8/2008 | |
| CN | 101856251 A | 10/2010 | |
| CN | 102028509 A | 4/2011 | |
| CN | 102247182 A | 11/2011 | |
| DE | 102008053842 A1 | 5/2010 | |
| EP | 0537570 A2 | 4/1993 | |
| EP | 0634144 A1 | 1/1995 | |
| EP | 0647431 A2 | 4/1995 | |
| EP | 0648476 A1 | 4/1995 | |
| EP | 0686374 A2 | 12/1995 | |
| EP | 0705571 A1 | 4/1996 | |
| EP | 0738501 A1 | 10/1996 | |
| EP | 1690502 A1 | 8/2006 | |
| EP | 1723913 A1 | 11/2006 | |
| EP | 1736112 A1 | 12/2006 | |
| EP | 1759652 A2 | 3/2007 | |
| EP | 1769754 A1 | 4/2007 | |
| EP | 1772105 A1 | 4/2007 | |
| EP | 1813199 A1 | 8/2007 | |
| EP | 1813203 A2 | 8/2007 | |
| EP | 1813207 A1 | 8/2007 | |
| EP | 1813211 A2 | 8/2007 | |
| EP | 1908412 A2 | 4/2008 | |
| EP | 1917929 A1 | 5/2008 | |
| EP | 1943954 A2 | 7/2008 | |
| EP | 1943956 A2 | 7/2008 | |
| EP | 1943958 A1 | 7/2008 | |
| EP | 1943976 A2 | 7/2008 | |
| EP | 1952769 A2 | 8/2008 | |
| EP | 2005898 A2 | 12/2008 | |
| EP | 2027819 A1 | 2/2009 | |
| EP | 2044890 A1 | 4/2009 | |
| EP | 2055243 A2 | 5/2009 | |
| EP | 2090247 A1 | 8/2009 | |
| EP | 2098170 A2 | 9/2009 | |
| EP | 2100561 A2 | 9/2009 | |
| EP | 2100562 A2 | 9/2009 | |
| EP | 2165664 A2 | 3/2010 | |
| EP | 2236098 A2 | 10/2010 | |
| EP | 2245994 A1 | 11/2010 | |
| EP | 2263568 A2 | 12/2010 | |
| EP | 2272443 A1 | 1/2011 | |
| EP | 2316345 A1 | 5/2011 | |
| EP | 2324776 A2 | 5/2011 | |
| EP | 2329773 A1 | 6/2011 | |
| EP | 2333509 A1 | 6/2011 | |
| EP | 2377472 A1 | 10/2011 | |
| EP | 2462878 A1 | 6/2012 | |
| EP | 2462880 A2 | 6/2012 | |
| EP | 2491872 A1 | 8/2012 | |
| EP | 2586382 A2 | 5/2013 | |
| EP | 2606834 A2 | 6/2013 | |
| EP | 2668910 A2 | 12/2013 | |
| EP | 2676615 A2 | 12/2013 | |
| EP | 2777518 A1 | 9/2014 | |
| EP | 2815705 A1 | 12/2014 | |
| EP | 2942028 A1 | 11/2015 | |
| ES | 2333509 A1 | 2/2010 | |
| FR | 2861574 A1 | 5/2005 | |
| JP | H0347249 A | 2/1991 | |
| JP | 08038488 | 2/1996 | |
| JP | 2005125075 A | 5/2005 | |
| JP | 2010253272 A | 11/2010 | |
| JP | 2011078772 A | 4/2011 | |
| JP | 2011224368 A | 11/2011 | |
| KR | 20120022521 A | 3/2012 | |
| WO | 9729694 A1 | 8/1997 | |
| WO | 9740760 A1 | 11/1997 | |
| WO | 9915086 A1 | 4/1999 | |
| WO | 1999/52489 A1 | 10/1999 | |
| WO | 0072760 A1 | 12/2000 | |
| WO | 0072765 A1 | 12/2000 | |
| WO | 03000138 A2 | 1/2003 | |
| WO | 03026511 A1 | 4/2003 | |
| WO | 03030743 A2 | 4/2003 | |
| WO | 03065916 A1 | 8/2003 | |
| WO | 03077769 A1 | 9/2003 | |
| WO | 03090630 A2 | 11/2003 | |
| WO | 2004/032760 A2 | 4/2004 | |
| WO | 2004107989 A1 | 12/2004 | |
| WO | 2006042210 A2 | 4/2006 | |
| WO | 2007016290 A2 | 2/2007 | |
| WO | 2007/026354 A1 | 3/2007 | |
| WO | 2007030753 A2 | 3/2007 | |
| WO | 2007118179 A2 | 10/2007 | |
| WO | 2007137304 A2 | 11/2007 | |
| WO | 2008131362 A2 | 10/2008 | |
| WO | 2008133956 A2 | 11/2008 | |
| WO | 2009039506 A1 | 3/2009 | |
| WO | 2007014355 A3 | 4/2009 | |
| WO | 2009132359 A2 | 10/2009 | |
| WO | 2009143092 A1 | 11/2009 | |
| WO | 2009149234 A1 | 12/2009 | |
| WO | 2011108840 A2 | 9/2011 | |
| WO | 2012/040984 A1 | 4/2012 | |
| WO | 2016171947 A1 | 10/2016 | |

OTHER PUBLICATIONS

Partial European Search Report corresponding to EP No. 13 17 1742.3, completed Sep. 17, 2013 and dated Sep. 25, 2013; (8 pp).

Partial European Search Report corresponding to EP No. 13 17 2400.7, completed Sep. 18, 2013 and dated Oct. 2013; (7 pp).

Extended European Search Report corresponding to EP No. 13 17 5475.6, completed Sep. 23, 2013 and dated Oct. 2013; (8 pp).

Extended European Search Report corresponding to EP No. 13 17 5478.0, completed Sep. 24, 2013 and dated Oct. 2, 2013; (6 pp).

Extended European Search Report corresponding to EP No. 13 17 5479.8, completed Sep. 27, 2013 and dated Oct. 10, 2013; (7 pp).

Partial Extended European Search Report corresponding to EP 13 17 5477.2, completed Oct. 7, 2013 and dated Oct. 15, 2013; (7 pp).

Extended European Search Report corresponding to EP No. 08 25 2703.7, completed Oct. 23, 2008 and dated Oct. 31, 2008; (7 pp).

European search Report from Appl. No. 13177163.6 dated Nov. 15, 2013. (8 pp).

Extended European Search Report from EP Application No. 13172400.7 dated Jan. 21, 2014.

Extended European Search Report from EP Application No. 13189026.1 dated Jan. 31, 2014.

The extended European Search Report from Application No. EP 13177163.6 dated Feb. 6, 2014.

Extended European Search Report from Application No. EP 13175477.2 dated Feb. 6, 2014.

Extended European Search Report from Application No. EP 13169998.5 dated Feb. 24, 2014.

Extended European Search Report corresponding to EP 13176805. 3, dated Nov. 4, 2013.

Extended European Search Report from Application No. EP 13171742.3 dated Jan. 3, 2014.

European Search Report dated Dec. 1, 2016, issued in EP Application No. 06771999.

European Search Report No. 13189650.8 dated Sep. 10, 2014.

European Search Report No. 14185097.4 dated Jan. 27, 2015.

(56) References Cited

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837 dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action dated Oct. 24, 2017 in corresponding Chinese Patent Application No. 201410479971.9 together with English translation, 12 pages.
Australian Examination Report dated Apr. 26, 2018 in corresponding Australian Patent Application No. 2014218366.
Australian Examination Report dated May 14, 2018 in corresponding Australian Patent Application No. 2014218361.
Japanese Office Action dated May 17, 2018 in corresponding Japanese Patent Application No. 2014-187528, together with English translation.
European Search Report dated Apr. 17, 2007 for Corresponding Patent Application EP06026840.
International Search Report for corresponding PCT Application—PCTIUS06/2I 524—dated May 28, 2008 (4 Pages).
Detemple, P., "Microtechnology in Modern Health Care", Med Device Technol. 9(9):18-25 (1998).
European Search Report for corresponding EP 08252703.7 dated Oct. 31, 2008 (3 pages).
European Search Report dated Feb. 27, 2009 for Corresponding Patent Application 08253-184.9.
European Search Report for corresponding EP 08252703.7 dated Oct. 11, 2008 (7 pages).
International Search Report corresponding to PCT/US2005/027266, completed May 30, 2008 and dated Jun. 18, 2008; (2 pp.).
Extended European Search Report corresponding to EP 08 25 2703.7, completed Oct. 23, 2008 and dated Oct. 31, 2008; (7 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Office Action dated Oct. 16, 2018 issued in corresponding EP Appln. No. EP18172025.

* cited by examiner

ADAPTIVE POWERED STAPLING ALGORITHM WITH CALIBRATION FACTOR

CROSS-REFERENCE TO RELATED APPLICATIONS

This application claims the benefit of and priority to U.S. Provisional Patent Application No. 62/506,180, filed May 15, 2017, the entire disclosure of which is incorporated by reference herein.

BACKGROUND

1. Technical Field

The present disclosure relates to surgical devices. More specifically, the present disclosure relates to handheld electromechanical surgical systems for performing surgical procedures having reusable components.

2. Background of the Related Art

Linear clamping, cutting and stapling devices are used in surgical procedures, for example to resect cancerous or anomalous tissue from a gastro-intestinal tract. Conventional clamping, cutting and stapling instruments include a pistol grip-styled structure having an elongated shaft and an end effector having a pair of gripping members disposed at a distal end of the shaft to clamp, cut, and staple tissue. Conventional stapling instruments may also include end effectors having circular stapler attachments. Actuation of the gripping members is usually accomplished by actuating a trigger coupled to the handle, in response to which one of the two gripping members, such as the anvil portion, moves or pivots relative to the elongated shaft while the other gripping element remains fixed. The fixed gripping member includes a staple cartridge and a mechanism for ejecting the staples through the clamped tissue against the anvil portion, thereby stapling the tissue. The end effector may be integrally formed with the shaft or may be detachable allowing for interchangeability of various gripping and stapling members.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures, and transverse anastomosis procedures, are actuated by a linear driving force. As such, these end effectors are not compatible with surgical devices and/or handle assemblies that use rotary motion.

Thus, there is a need to ensure compatibility between various systems and as well as ensure proper functionality of all of the drive components based on mechanical limitations of the system as a whole.

SUMMARY

According to one embodiment of the present disclosure, a surgical system includes: an adapter assembly; an end effector configured to couple to a distal portion of the adapter assembly; and a surgical device configured to couple to a proximal portion of the adapter assembly. The surgical device includes: a power source; a motor coupled to the power source, the motor configured to actuate at least one of the adapter assembly or the end effector; and a controller operatively coupled to the motor and configured to calibrate the motor while at least one of the adapter assembly or the end effector is actuated by the motor.

According to one aspect of the above embodiment, the surgical system further includes: a force sensor coupled to at least one of the adapter assembly, the end effector, or the motor, and the force sensor is configured to measure a force imparted on at least one of the adapter assembly, the end effector, or the motor.

According to another aspect of the above embodiment, the force sensor is coupled to the controller and is configured to provide a force measurement signal indicative of the force.

According to a further aspect of the above embodiment, the surgical device further includes a memory coupled to the controller that is configured to store calibration data in the memory based on the force measurement signal. The controller is further configured to operate the motor based on the calibration data.

According to one aspect of the above embodiment, the adapter assembly includes a first storage device, which stores a first value corresponding to operation of the adapter assembly. The controller is further configured to read the first value and to adjust the first value based on the calibration data to obtain an adjusted first value and to operate the motor based on the adjusted first value.

According to another aspect of the above embodiment, the end effector includes a second storage device, which stores a second value corresponding to operation of the adapter assembly. The controller is further configured to read the second value and to adjust the second value based on the calibration data to obtain an adjusted second value and the controller is configured to operate the motor based on the adjusted second value.

According to another embodiment of the present disclosure, a method for controlling a surgical system includes: coupling an adapter assembly to a surgical device; coupling an end effector to the adapter assembly; energizing a motor of the surgical device to actuate at least one of the adapter assembly or the end effector; measuring a parameter associated with actuation of at least one of the adapter assembly or the end effector; and calibrating the motor based on the parameter associated with the actuation of at least one of the adapter assembly or the end effector.

According to one aspect of the above embodiment, the measurement of the parameter is performed by a force sensor coupled to at least one of the adapter assembly, the end effector, or the motor. The measurement of the parameter includes measuring a force imparted on at least one of the adapter assembly, the end effector, or the motor, the force sensor.

According to another aspect of the above embodiment, the method further includes transmitting a force measurement signal indicative of the force to a controller.

According to a further aspect of the above embodiment, the method further includes storing calibration data in a memory coupled to the controller based on the force measurement signal; operating the motor based on the calibration data; reading a value corresponding to operation of at least one of the end effector or the adapter assembly from a storage device associated with at least one of the end effector or the adapter assembly; and operating the motor based on the value adjusted by the calibration data.

DESCRIPTION OF THE DRAWINGS

Embodiments of the present disclosure are described herein with reference to the accompanying drawings, wherein.

DETAILED DESCRIPTION

Figure 1:
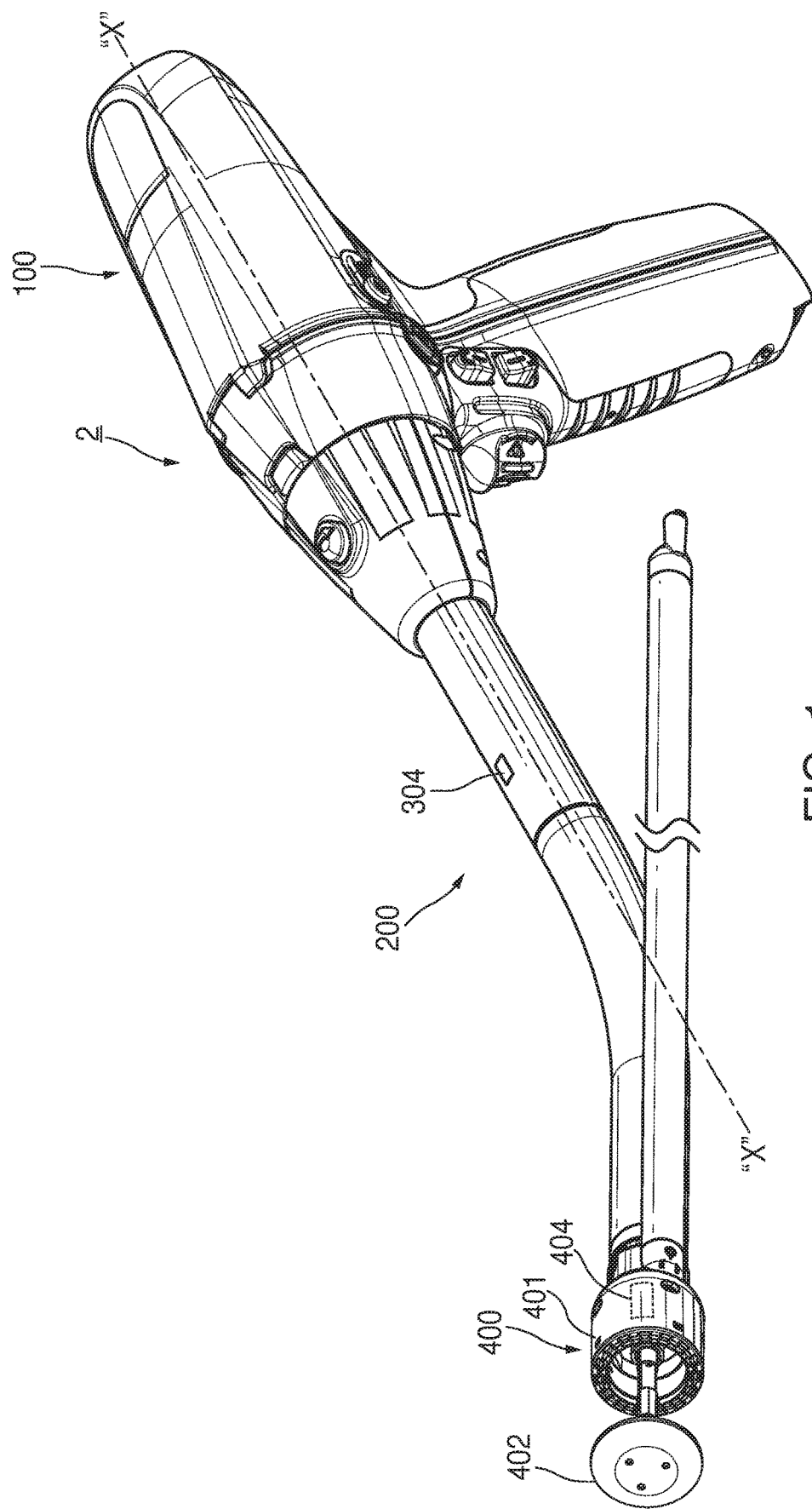
FIG. 1 is a perspective view of a surgical system including a handheld surgical device, an adapter assembly, and a circular stapler end effector according to an embodiment of the present disclosure.

Embodiments of the presently disclosed surgical devices and adapter assemblies for use with the surgical devices are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

The present disclosure provides a powered surgical device including one or more motors configured to actuate a surgical end effector coupled to the surgical device via an adapter assembly. More specifically, the powered surgical device is configured to couple to an adapter assembly, which in turn, couples to the end effector. One or more force sensors are embedded in one or more of the surgical device, the adapter assembly, and/or the end effector and are configured to monitor the forces imparted on various mechanical components of each of them. The force sensors are configured to provide force measurements to a controller of the surgical device, which then utilizes the measured force to calibrate operation of its motors.

The surgical device according to the present disclosure is configured to monitor the position of various mechanical components, e.g., those of surgical device, the adapter, and the end effector. The powered surgical device is also configured to monitor and react accordingly to forces measured during usage by a force sensor. In particular, the powered surgical device implements an adaptive stapling algorithm executable by the controller in which the surgical device monitors mechanical forces and adjusts the motor speed in response thereto. Execution of the algorithm decreases the motor speed to reduce forces and thus can provide benefits such as improved reliability, better staple formation, and stronger staple lines to reduce leaks. The algorithm may also utilize a shut off force value utilized by the controller to ensure proper functionality of the surgical device without exceeding mechanical limits of the system (e.g., powered surgical device, adapter assembly, and end effector) as a whole.

The powered surgical device according to the present disclosure is also configured to perform force calibration of the powered surgical device, adapter assembly, and/or end effector, which allows for quantifying inherent forces seen within the surgical system that are specific to the components (e.g., adapter assembly and end effector) being used. The measured force is used as a delta factor by the motor control algorithm during the stapling process. The delta factor encompasses variables associated with each of the components of the system, such as the type of the end effector, movement of the end effector, articulation angle, type of tissue, and reloads inclusive of a buttress reinforcement material, and the like. This allows the powered surgical device to incorporate such factors into its motor control algorithm as well as adjust the acceptable force range and/or motor movement based on this factor.

As illustrated in FIG. 1, a surgical system 2 according to the present disclosure includes a surgical device 100, which is shown as a powered hand held electromechanical instrument, configured for selective attachment to a plurality of different types of end effectors 400 having a circular stapler reload 401 and anvil 402. In particular, surgical device 100 is configured for selective connection with an adapter 200, and, in turn, adapter 200 is configured for selective connection with the end effector 400.

Figure 2:
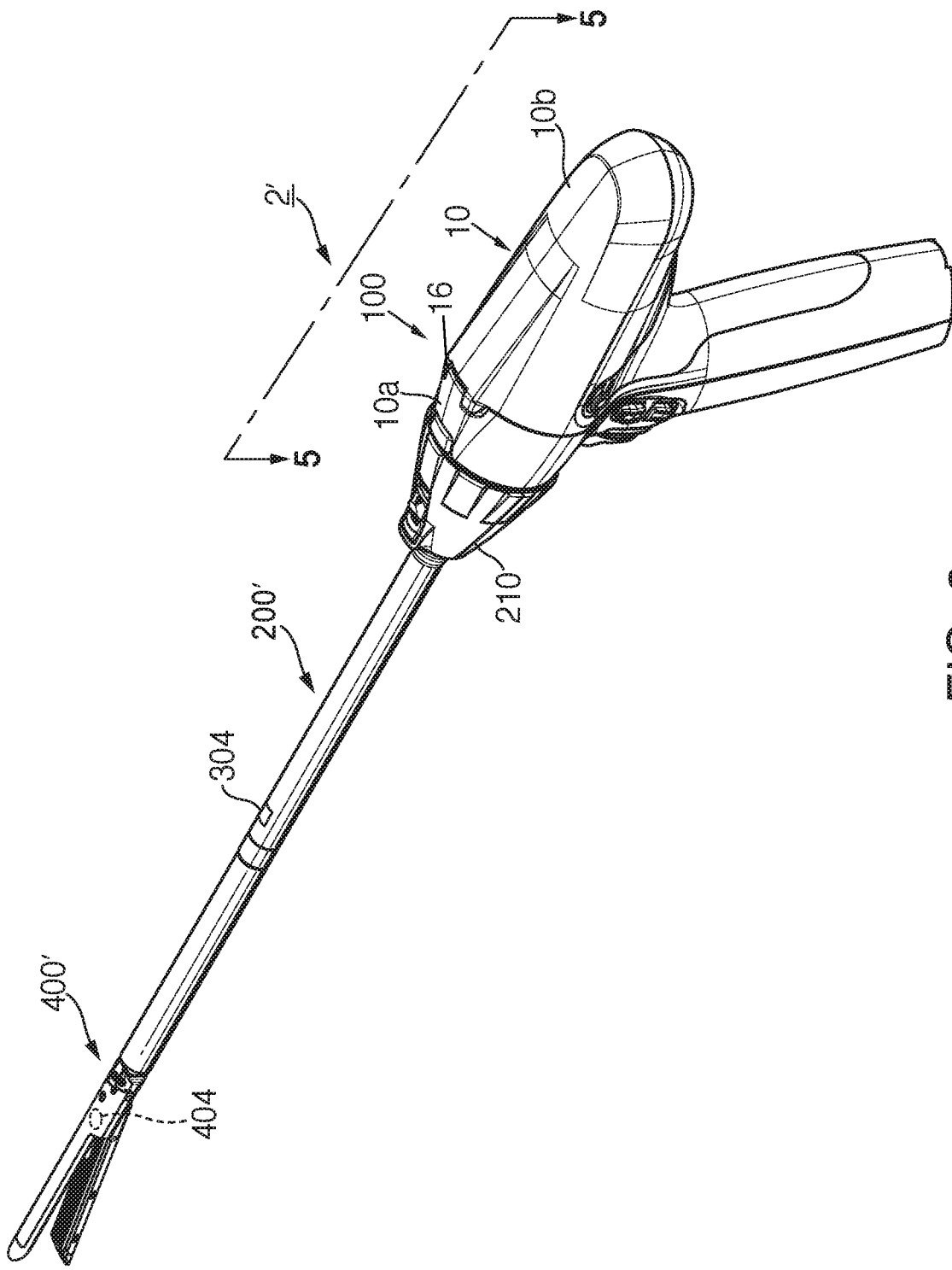
FIG. 2 is a perspective view of a surgical system including the handheld surgical device of FIG. 1, an adapter assembly, and a linear stapler end effector according to another embodiment of the present disclosure.

FIG. 2 illustrates another embodiment of a surgical system 2' which also includes the surgical device 100 of FIG. 1, but utilizes a different type of an adapter 200' that is suitable for use with end effectors 400' or single use loading units ("SULU's"), such as a linear stapler end effectors. Thus, the surgical device 100 is configured to operate with a variety of types of end effectors 400 or 400' and corresponding adapters 200 or 200'.

With reference to FIGS. 2-5, surgical device 100 includes a power-pack 101 (FIG. 3), and an outer shell housing 10 (FIG. 2) configured to selectively receive and enclose the power-pack 101. Outer shell housing 10 includes a distal half-section 10a and a proximal half-section 10b. The proximal half-section 10b pivotably connected to distal half-section 10a by a hinge 16 located along an upper edge of distal half-section 10a and proximal half-section 10b such that distal and proximal half-sections 10a, 10b are divided along a plane that traverses a longitudinal axis defined by adapter 200. When joined, distal and proximal half-sections 10a, 10b define a shell cavity 10c (FIG. 3) for receiving power-pack 101.

Figure 3:
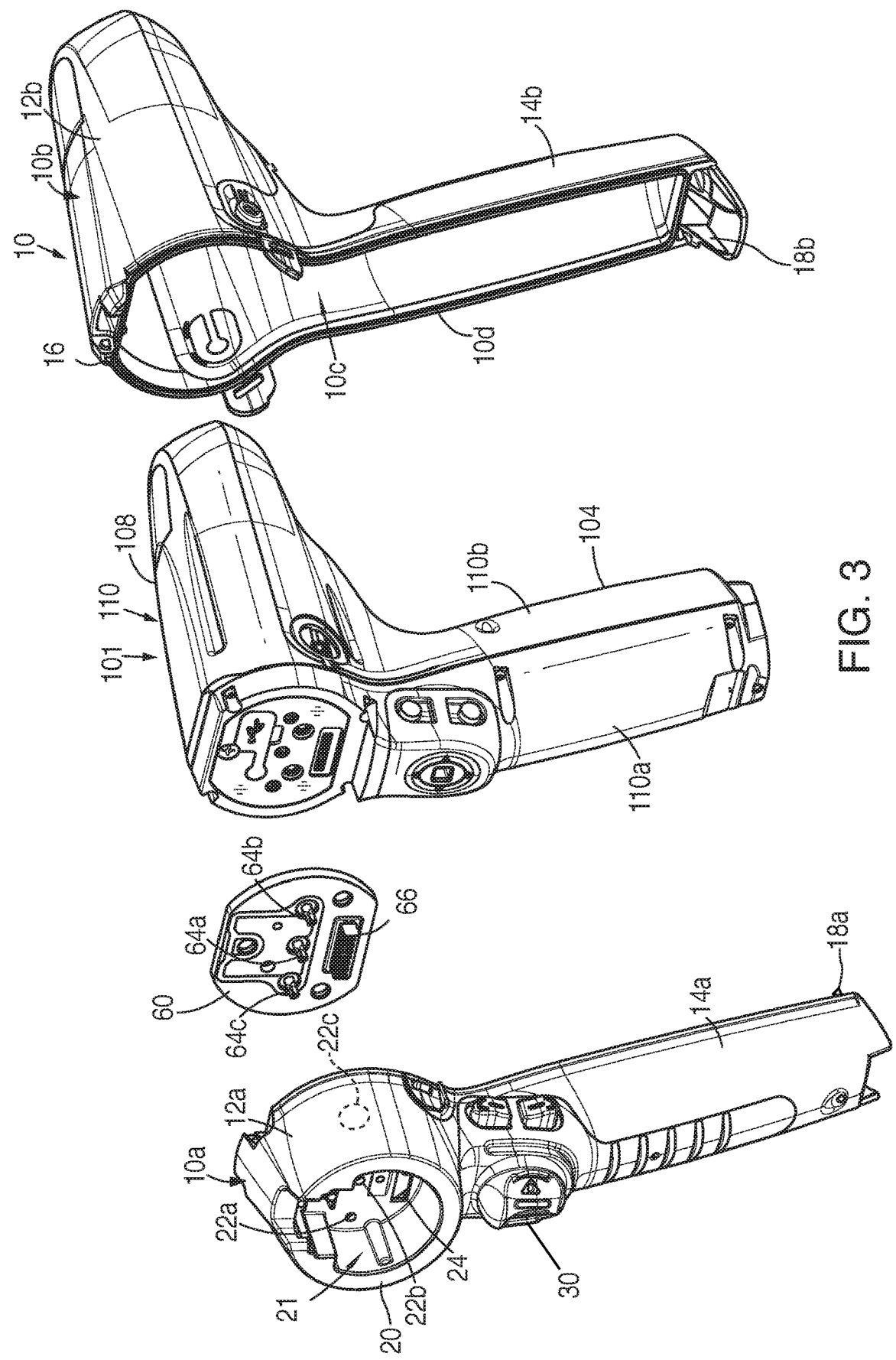
FIG. 3 is a front perspective view, with parts separated, of the handheld surgical device of FIG. 1.

With reference to FIG. 3, each of distal and proximal half-sections 10a, 10b includes a respective upper shell portion 12a, 12b, and a respective lower shell portion 14a, 14b. Lower shell portion 14a includes a closure tab 18a configured to engage a closure tab 18b of the lower shell portion 14b to selectively secure distal and proximal half-sections 10a, 10b to one another and for maintaining shell housing 10 in a closed configuration.

Distal half-section 10a of shell housing 10 also includes a connecting portion 20 configured to couple to a corresponding drive coupling assembly 210 of adapter 200 (FIG.

6). Specifically, the connecting portion 20 includes a recess 21 configured to receive a portion of drive coupling assembly 210 of adapter 200 when adapter 200 is mated to surgical device 100. Connecting portion 20 of distal half-section 10a also defines three apertures 22a, 22b, 22c and an elongate slot 24 formed in a distally facing surface thereof.

Distal half-section 10a of shell housing 10 also includes a plurality of buttons such as a toggle control button 30. In embodiments, toggle control button 30 may be a two-axis control stick configured to be actuated in a left, right, up and down direction. The toggle control button 30 may also be depressible (e.g., along a third axis).

Distal half-section 10a of shell housing 10 may also support a plurality of other buttons such as a right-side pair of control buttons and a left-side pair of control button. These buttons and other components are described in detail in U.S. Patent Application Publication No. 2016/0310134, the entire disclosure of which is incorporated by reference herein.

With reference to FIG. 3, shell housing 10 includes a sterile barrier plate 60 removably supported in distal half-section 10a. The sterile barrier plate 60 interconnects the power-pack 101 and the adapter 200. Specifically, sterile barrier plate 60 is disposed behind connecting portion 20 of distal half-section 10a and within shell cavity 10c of shell housing 10. Plate 60 includes three coupling shafts 64a, 64b, 64c rotatably supported therein. Each coupling shaft 64a, 64b, 64c extends through a respective aperture 22a, 22b, 22c of connecting portion 20 of distal half-section 10a of shell housing 10.

Plate 60 further includes an electrical pass-through connector 66 supported thereon. Pass-through connector 66 extends through aperture 24 of connecting portion 20 of distal half-section 10a when sterile barrier plate 60 is disposed within shell cavity 10c of shell housing 10. Coupling shafts 64a, 64b, 64c and pass-through connector 66 electrically and mechanically interconnect respective corresponding features of adapter 200 and the power-pack 101.

During use, the shell housing 10 is opened (i.e., distal half-section 10a is separated from proximal half-section 10b about hinge 16), power-pack 101 is inserted into shell cavity 10c of shell housing 10, and distal half-section 10a is pivoted about hinge 16 to a closed configuration. In the closed configuration, closure tab 18a of distal half-section 10a engages closure tab 18b of proximal half-section 10b. Following a surgical procedure, shell housing 10 is opened and the power-pack 101 is removed from shell cavity 10c of shell housing 10. The shell housing 10 may be discarded and the power-pack 101 may then be disinfected and cleaned.

Figure 4:
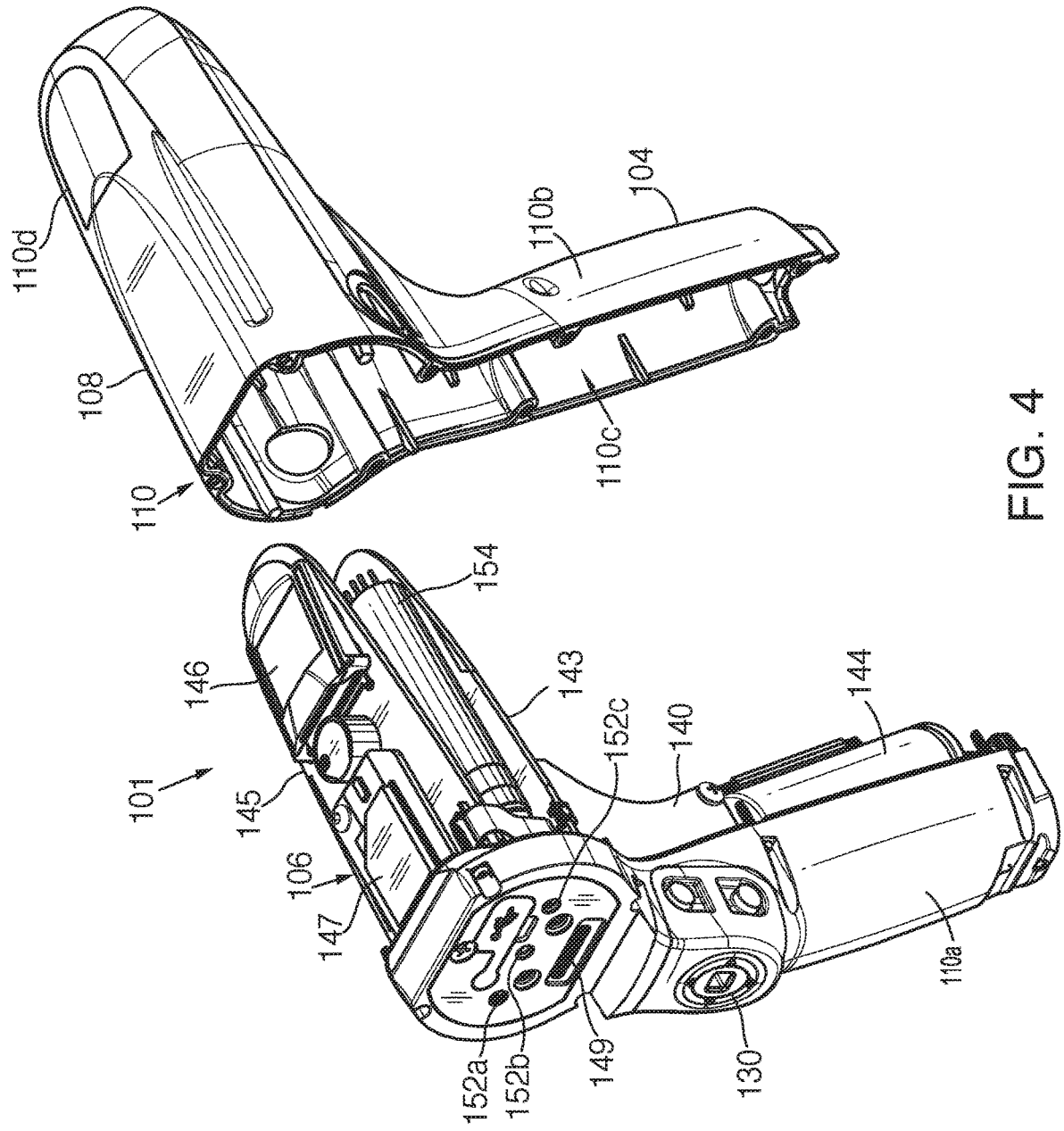
FIG. 4 is a front, perspective view of a power-pack and an inner rear housing of FIG. 3 separated therefrom.
Figure 5:
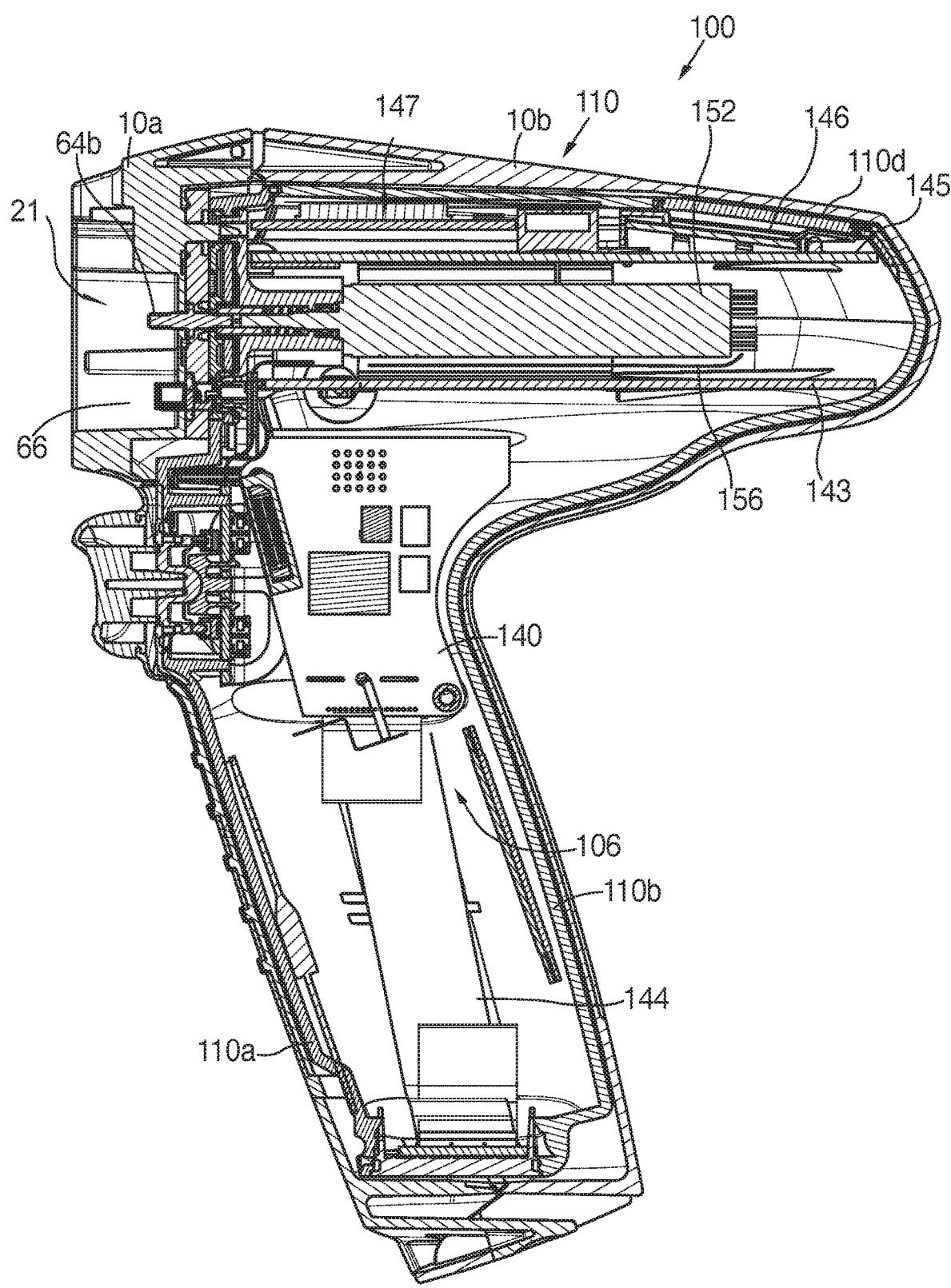
FIG. 5 is a cross-sectional view of the handheld surgical device of FIG. 2 taken along a section line "5-5" of FIG. 2.

Referring to FIGS. 3-5, power-pack 101 includes an inner handle housing 110 having a lower housing portion 104 and an upper housing portion 108 extending from and/or supported on lower housing portion 104. The inner handle housing 110 also includes a distal half-section 110a and a proximal half-section 110b, which define an inner housing cavity 110c (FIG. 4) for housing a power-pack core assembly 106 (FIG. 4). Power-pack core assembly 106 is configured to control the various operations of surgical device.

With reference to FIG. 4, distal half-section 110a of inner handle housing 110 supports a distal toggle control interface 130 that is operatively engaged with toggle control button 30 of shell housing 10, such that when power-pack 101 is disposed within shell housing 10, actuation of toggle control button 30 exerts a force on toggle control interface 130. Distal half-section 110a of inner handle housing 110 also supports various other control interfaces which operatively engage other buttons of shell housing 10.

With reference to FIGS. 4 and 5, power-pack core assembly 106 includes a battery circuit 140, a motor controller circuit 143, a main controller circuit 145, a main controller 147, and a rechargeable battery 144 configured to supply power to any of the electrical components of surgical device 100. Power-pack core assembly 106 further includes a display screen 146 supported on main controller circuit 145. Display screen 146 is visible through a clear or transparent window 110d disposed in proximal half-section 110b of inner handle housing 110.

Power-pack core assembly 106 further includes a first motor 152 (FIG. 5), a second motor 154 (FIG. 4), and a third motor 156 (FIG. 5) each electrically connected to controller circuit 143 and battery 144. Motors 152, 154, 156 are disposed between motor controller circuit 143 and main controller circuit 145. Each motor 152, 154, 156 is controlled by a respective motor controller (not shown) that are disposed on motor controller circuit 143 and are coupled to a main controller 147. The main controller 147 is also coupled to memory 141 (FIG. 8), which is also disposed on the motor controller circuit 143. The main controller 147 communicates with the motor controllers through an FPGA, which provides control logic signals (e.g., coast, brake, etc. and any other suitable control signals). The motor controllers output corresponding energization signals to their respective motors 152, 154, 156 using fixed-frequency pulse width modulation (PWM) or any other suitable control signals.

Power-pack core assembly 106 also includes an electrical receptacle 149. Electrical receptacle 149 is in electrical connection with main controller board 145 via a second ribbon cable (not shown). Electrical receptacle 149 defines a plurality of electrical slots for receiving respective electrical contacts extending from pass-through connector 66 of plate 60 (FIG. 3) of shell housing 10.

Each motor 152, 154, 156 includes a respective motor shaft 152a, 152b, 152c extending therefrom. Each motor shaft 152a, 152b, 152c may have a recess defined therein having a tri-lobe transverse cross-sectional profile for receiving proximal ends of respective coupling shaft 64a, 64b, 64c of plate 60 of shell housing 10.

Rotation of motor shafts 152a, 152b, 152c by respective motors 152, 154, 156 actuates shafts and/or gear components of adapter 200 in order to perform various operations of surgical device 100. In particular, motors 152, 154, 156 of power-pack core assembly 106 are configured to actuate shafts and/or gear components of adapter 200 in order to selectively actuate components of the end effector 400, to rotate end effector 400 about a longitudinal axis, and to pivot the end effector 400 about a pivot axis perpendicular to the longitudinal axis defined by the adapter 200.

Figure 6:
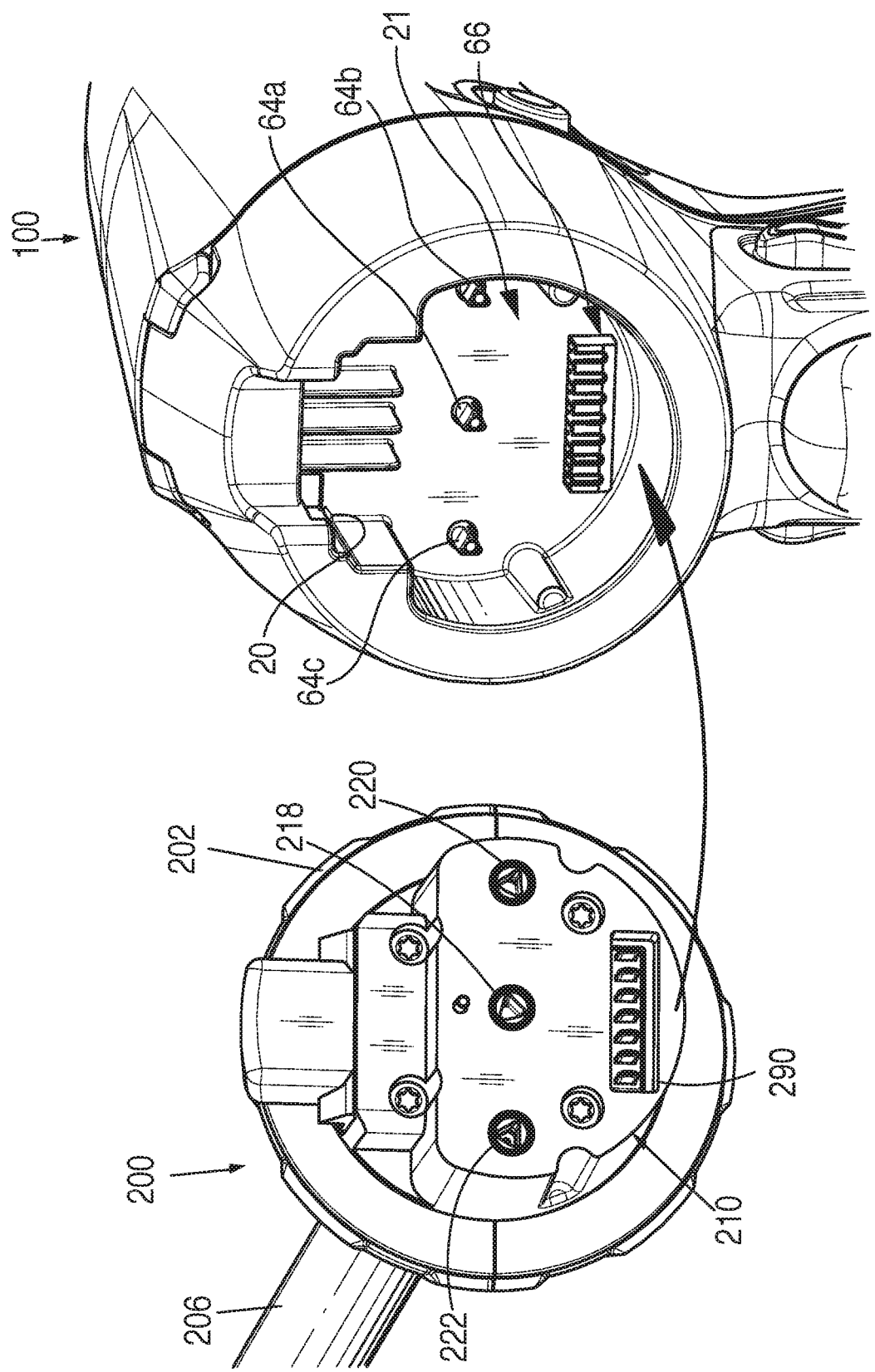
FIG. 6 is a perspective view of the adapter assembly of FIG. 1 separated from the handheld surgical device of FIG. 1 according to an embodiment of the present disclosure.
Figure 7:
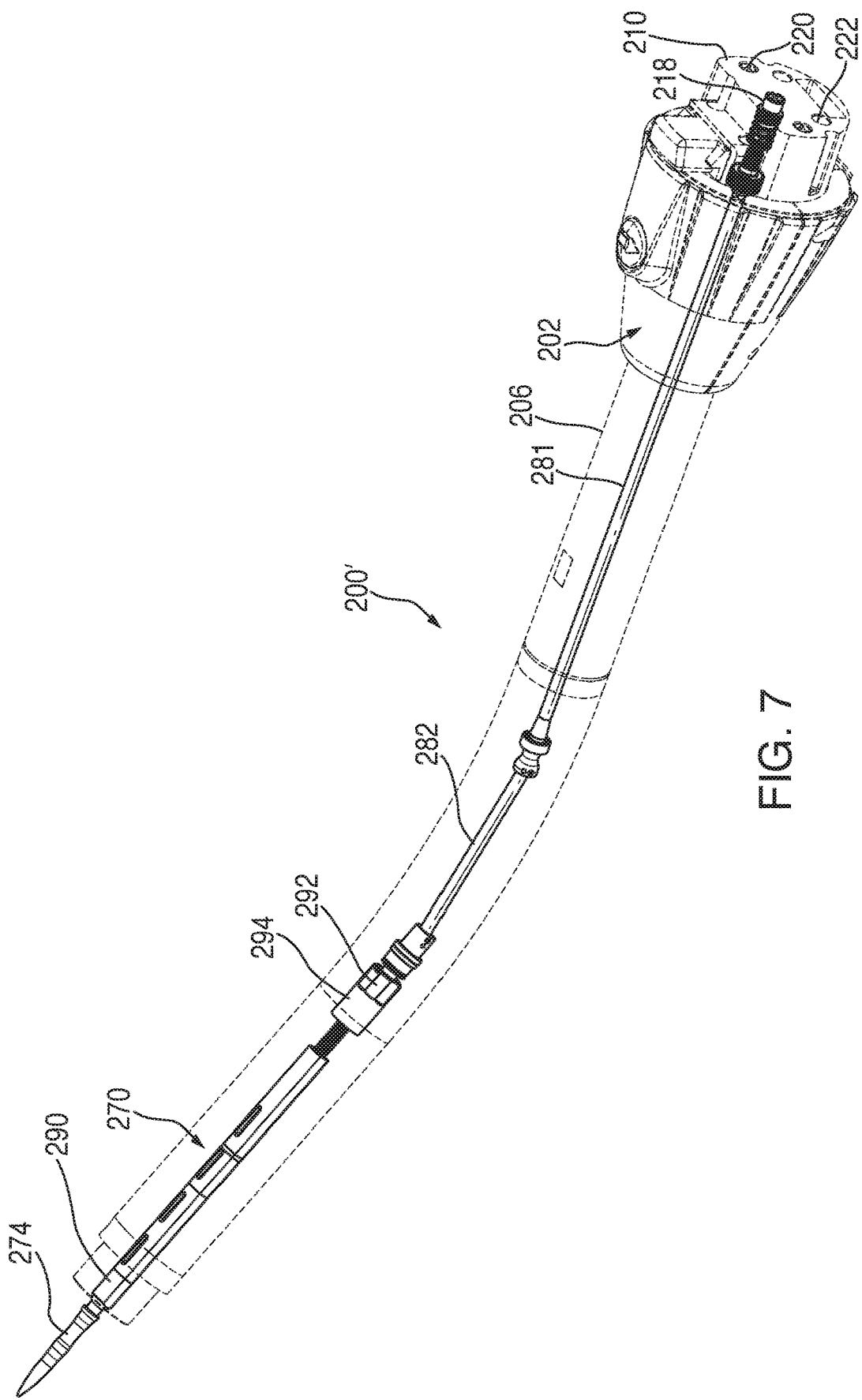
FIG. 7 is a perspective, partially-transparent view of the adapter assembly of FIG. 1 according to an embodiment of the present disclosure.

With reference to FIGS. 6 and 7, the adapter 200 includes an outer knob housing 202 and an outer tube 206 extending from a distal end of knob housing 202. Knob housing 202 is configured and adapted to connect to connecting portion 20 of shell housing 10 of surgical device 100 via the drive coupling assembly 210 as described above. The outer tube 206 is configured for selective connection with the end effector 400 (FIG. 1).

The drive coupling assembly 210 extends proximally from the knob housing 202 and includes a plurality of rotatable connector sleeves 218, 220, 222. The drive coupling assembly 210 is configured to couple to the recess 21 of the connecting portion 20 of the shell housing 10. The adapter 200' is configured to couple to the surgical device 100 in a similar manner. A connector 290 of the adapter assembly 200 is configured to mate with the pass-through connector 66 of the surgical device 100. Once the adapter 200 is mated to the surgical device 100, the coupling shafts 64a, 64b, 64c of the surgical device 100 engage the corresponding rotatable connector sleeves 218, 220, 222. Each of connector sleeves 218, 222, 220 is configured to interconnect respective first, second and third coupling shafts 64a, 64b, 64c of surgical device 100 with respective proximal drive shafts (not shown) of adapter 200. Each of the proximal drive shafts is configured to actuate various components of the adapter 200, the end effector 400, and/or the anvil 402.

With reference to FIG. 7, the connector sleeve 218 is coupled to a rotatable proximal drive shaft 281, which is in turn coupled to a second rotatable drive shaft 282, that is coupled to a trocar assembly 270. For brevity only the mechanical linkages coupled to the connector sleeve 218 are shown. The trocar assembly 270 is selectively couplable to a trocar member 274 or the anvil assembly 402. The adapter 200 also includes a force sensor 292 disposed in support block 294 that is fixedly coupled within the outer tube 206. The force sensor 292 is configured to measure and monitor forces imparted on the trocar member 274 during extension and retraction thereof. In addition, the force sensor 292 is also configured to monitor forces imparted on any other movable components of the adapter 200 that are mechanically coupled to the force sensor 292. The force sensor 292 is coupled to the main controller 147 of the surgical device 100 using a wired or a wireless connection. A wired connection may be any suitable wired interface (e.g., 1-wire) through the connector 290 and the pass-through connector 66. Wireless connection may be implemented any suitable electromagnetic wave communication protocol, such as BLUETOOTH®, near-field communication protocols, radio-frequency identification protocols, and the like. In embodiments, the force sensor 292 may be disposed within the adapter assembly 200', the end effectors 400 or 400', and/or the surgical device 100.

Figure 8:
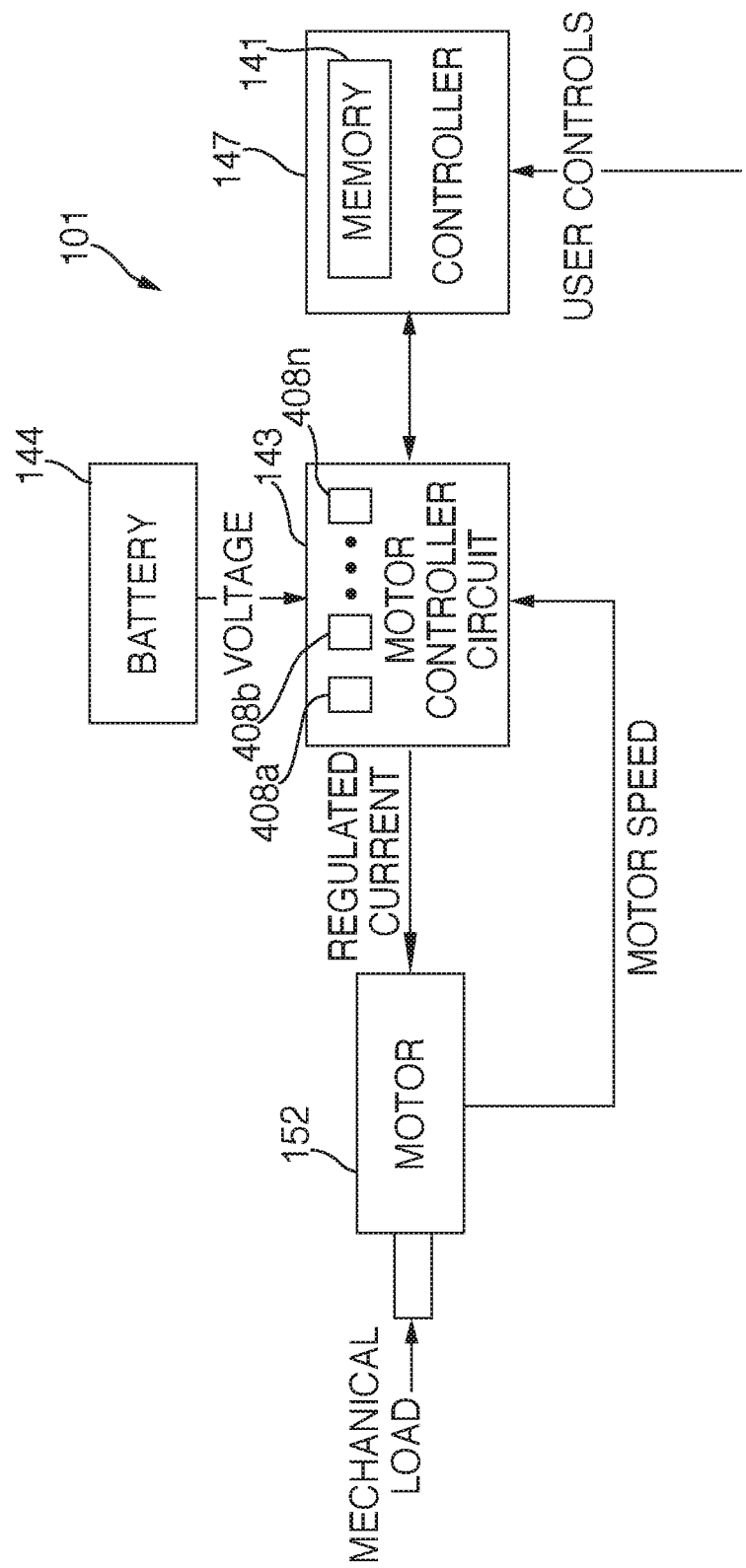
FIG. 8 is a schematic diagram of the handheld surgical device of FIG. 1 according to the present disclosure.

With reference to FIG. 8, a schematic diagram of the power-pack 101 is shown. For brevity, only one of the motors 152, 154, 156 is shown, namely, motor 152. The motor 152 is coupled to the battery 144. In embodiments, the motor 152 may be coupled to any suitable power source configured to provide electrical energy to the motor 152, such as an AC/DC transformer.

The battery 144 and the motor 152 are coupled to the motor controller circuit 143 which controls the operation of the motor 152 including the flow of electrical energy from the battery 144 to the motor 152. The motor controller circuit 143 includes a plurality of sensors 408a, 408b, . . . 408n configured to measure operational states of the motor 152, the battery 144, or any other components of the system 2. The sensors 408a-n may include the force sensor 290, voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152. Position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller circuit 143 and/or the controller 147 may measure time and process the above-described values as a function thereof, including integration and/or differentiation, e.g., to determine the rate of change in the measured values.

The motor controller circuit 143 is also coupled to the controller 147, which includes a plurality of inputs and outputs for interfacing with the motor controller circuit 143. In particular, the controller 147 receives measured sensor signals from the motor controller circuit 143 regarding operational status of the motor 152 and the battery 144 and, in turn, outputs control signals to the motor controller circuit 143 to control the operation of the motor 152 based on the sensor readings and specific algorithm instructions, which are discussed in more detail below. The controller 147 is also configured to accept a plurality of user inputs from a user interface (e.g., switches, buttons, touch screen, etc. coupled to the controller 147).

With reference to FIGS. 1, 2, and 8, each of the end effectors 400 or 400' include a storage device 404 which stores data pertaining to the end effector 400 or 400', respectively. The storage device 404 may include non-volatile storage medium (e.g., EEPROM) that is configured to store any data pertaining to the end effector 400 or 400', including but not limited to, usage count, identification information, model number, serial number, staple size, stroke length, maximum actuation force, minimum actuation force, factory calibration data, and the like.

With continued reference to FIGS. 1 and 2, each of the adapters 200 and 200' also include a storage device 304, similar to the storage device 404. The storage device 304 is configured to store any data pertaining to the adapters 200 and 200', including but not limited to, designation of which of the rotatable connector sleeves 218, 220, 222 correspond to specific functions of the end effector 400 or 400' (e.g., mapping connector sleeves 218, 220, 222 to functions), usage count, identification information, model number, serial number, identification information, model number, serial number, maximum and/or minimum actuation force for each of the rotatable connector sleeves 218, 220, 222, factory calibration data, and the like.

The storage devices 304 and 404 are configured to communicate with the main controller 147 of the surgical device 100 using a wired or a wireless connection. A wired connection may be any suitable wired interface (e.g., 1-wire) through the connector 290 and the pass-through connector 66. In embodiments, the storage devices 304 and 404 may also be used to authenticate the attached component, e.g., the adapter 200 or 200', the end effector 400 or 400'.

The present disclosure provides for an apparatus and method for controlling the surgical device 100 or any other powered surgical instrument, including, but not limited to, linear powered staplers, circular or arcuate powered staplers, graspers, electrosurgical sealing forceps, rotary tissue morcellating devices, and the like. In particular, the surgical device 100 is configured to adjust the speed of the motor 152 based on force measurements, including calibration, from the force sensor 292. The force feedback may be utilized during any operation of the motor 152, e.g., whether the motor 152 is actuating articulation of the end effector 400', ejecting staples from the end effector 400 or 400', moving the anvil 402, etc. In addition, to using continuous force feedback during operation of the motor 152, the surgical device 100 is also configured to calibrate the motor 152 based on the adapter 200 or 200' along with the end effector 400 or 400' to account for inherent mechanical losses associated with each individual component attached to the surgical device 100 (e.g., adapter 200 or 200', the end effector 400 or 400'). In embodiments, the surgical device 100 may also utilize calibration data stored on the storage device 304 and/or storage device 404. The calibration data may be used in conjunction with force calibration performed by the surgical device 100 as described in further detail below.

Figure 9:
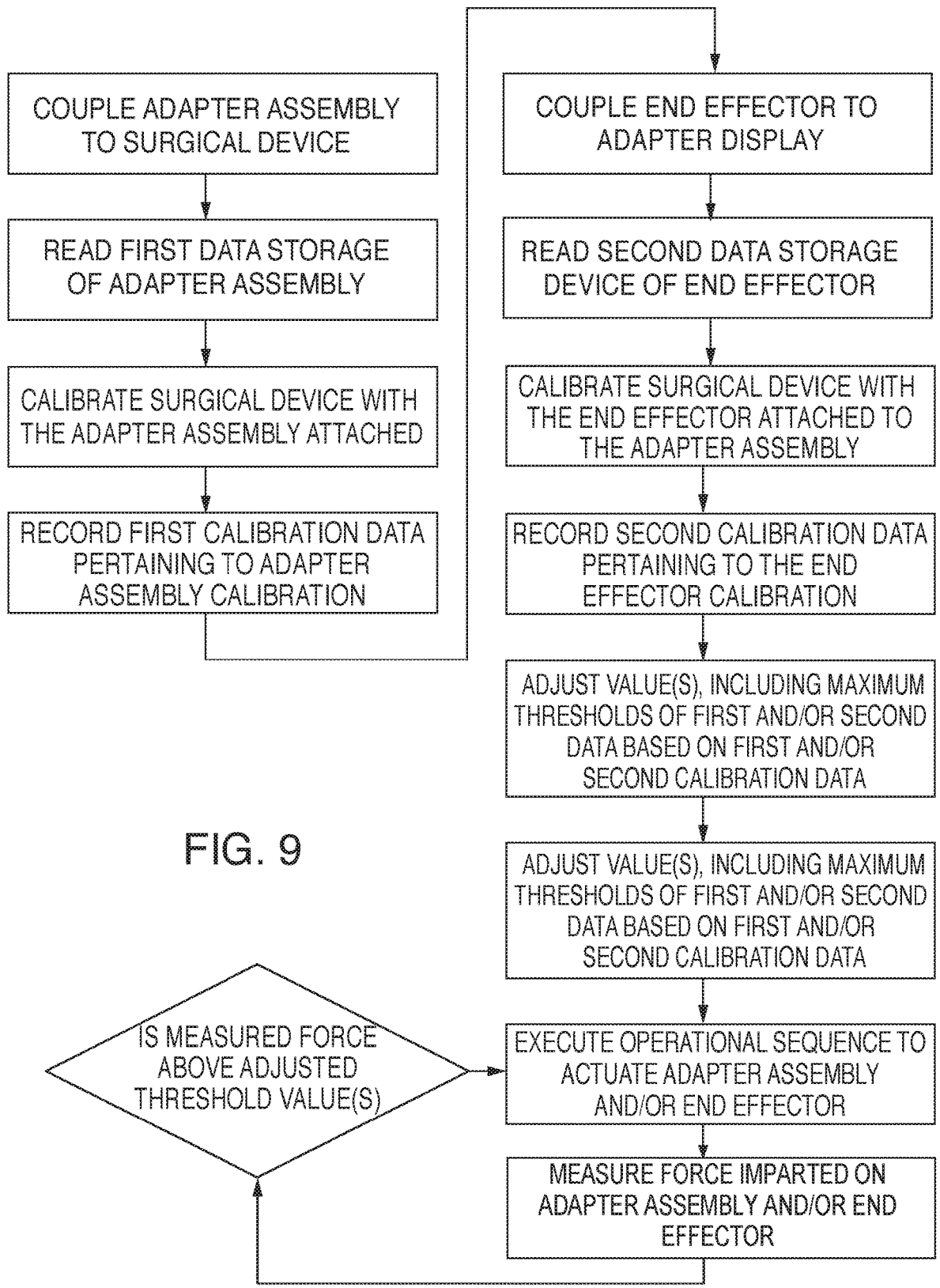
FIG. 9 is a flow chart of a method for controlling the handheld surgical device of FIG. 1 according to an embodiment of the present disclosure.

FIG. 9 shows a method according to the present disclosure of operating the surgical device 100. The method is described below with respect to the adapter 200 and the end effector 400, but is applicable with respect to adapter 200' and the end effector 400' or any other suitable attachments. Initially, the adapter 200 is coupled to the surgical device 100. The surgical device 100, and namely, main controller 147 verifies that the adapter 200 is authentic based on the data stored on the storage device 304. After verification, the main controller 147 may also read additional data from the storage device 304, such as calibration data, maximum actuation force data, etc.

The main controller 147 commences a first calibration process for the adapter 200. This includes actuating each of the coupling shafts 64a, 64b, 64c to rotate connector sleeves 218, 222, 220 and their corresponding drive trains. While each of the connector sleeves 218, 222, 220 are actuated, the force sensor 292 measures force imparted on the drive trains. Calibration may include obtaining a reference force measurement while driving the connector sleeves 218, 222, 220 in a first direction until their respective mechanical limits are reached and then returning the connector sleeves 218, 222, 220 back to their starting position or until another mechanical limit is reached. In embodiments, each or all of the connector sleeves 218, 222, 220 may be calibrated. The encountered force for each of the mechanical limits of the connector sleeves 218, 222, 220 is stored in the memory 141. In addition, the main controller 147 also records the force imparted on the drive trains of the adapter 200 for the duration of calibration, namely, the force associated while the connector sleeves 218, 222, 220 are actuated between mechanical limits. Since the adapter 200 is not acting on any mechanical loads, e.g., the end effector 400 and/or tissue, the measured force corresponds to the force required to drive only the components of the adapter 200, which is stored as a first (e.g., adapter) force calibration data.

After the calibration of the adapter 200, the end effector 400 is coupled to the adapter 200. The surgical device 100, and namely, main controller 147 verifies that the end effector 400 is authentic based on the data stored on the storage device 404. After verification, the main controller 147 may also read additional data from the storage device 404, such as calibration data, maximum actuation force data, etc.

The main controller 147 commences a second calibration process for the end effector 400 and/or the anvil 402. This includes actuating each of the coupling shafts 64a, 64b, 64c to rotate connector sleeves 218, 222, 220 and their corresponding drive trains while the end effector 400 and/or the anvil 402 are attached to the adapter 200. While each of the connector sleeves 218, 222, 220 are actuated, the force sensor 292 measures the forces imparted on the drive trains while actuating the end effector 400 and/or the anvil 402. Calibration may include obtaining reference force measurements while driving the connector sleeves 218, 222, 220 in a first direction until mechanical limits of the end effector 400 and/or the anvil 402 are reached and then returning the articulation shaft back to the starting position or until another mechanical limit is reached. The encountered force for each of the mechanical limits is stored in the memory 141. In addition, the main controller 147 also records the force imparted on the drive trains of the adapter 200 for the duration of calibration, namely, the force associated while the end effector 400 and/or the anvil 402 are actuated between mechanical limits. Since during the second calibration the adapter 200 is actuating the end effector 400 and/or the anvil 402, the measured force corresponds to the combined force that is used to drive various components of the adapter 200 as well as those of the end effector 400 and/or the anvil 402, which is stored as a second (e.g., combined) force calibration data.

In embodiments, the first and second calibration processes may be performed as a single sequence, namely, the first calibration may be omitted and combined with the second calibration, such that a single calibration occurs after the adapter 200 is coupled to the surgical device 100, and the end effector 400 with the anvil 402 is coupled to the adapter 200) to obtain the combined force calibration data. In further embodiments, the controller 147 may determine the calibration data for the end effector 400 and/or the anvil 402 based on the difference between the first and second calibration data.

The controller 147 also uses the first and/or second force calibration data to adjust values loaded from the storage device 304 and/or 404. In addition to the values loaded from the storage device 304 and/or 404, the controller 147 also uses the first and/or second force calibration data to adjust threshold values stored in memory 141. Each of the individual sequences (e.g., cutting, stapling, articulation, etc.) may include a plurality of corresponding force threshold values. The threshold values are stored in the memory 141 and are used by the controller 147 to control each of the sequences. One of the threshold values may be a maximum force value beyond which operation of the motor 152 may result in damage to the surgical device 100, the adapter 200, end effector 400, and/or anvil 402. In embodiments, each one of these components may have its own individual maximum threshold force value that may be stored in the storage device 304 or 404, respectively, and read by the controller 147 as described above.

The controller 147 uses the measured first and/or second calibration data to adjust the stored threshold values in memory 141. Adjustment of threshold values may include using the calibration data to derive offset values, which are then used to modify the threshold values. Offset values derived from the calibration data may then be used to adjust the threshold values by using any suitable mathematical function defining the relationship between calibration data and threshold values.

Once calibration is performed and the threshold values are updated based on the first and and/or second calibration data, the system 2 may be used to perform the surgical procedure. The motor 152 is energized to actuate various components of the adapter 200 as well as the end effector 400 and/or anvil 402 based on user's input commands. During operation, the force is continuously measured by the force sensor 292. The collected force data is utilized to control the stapling, cutting, articulation, and any other sequences that the surgical device 100 is programmed to perform. In embodiments, the force thresholds may be used to execute specific functions and/or subsequences used during certain operational sequences, such as a first threshold may be used to determine whether a clamping sequence is complete, a second threshold may be used to determine if a stapling sequence is complete, and a third threshold may be used to determine if a cutting sequence is complete.

In embodiments, the controller 147 may also continuously compare measured force from the force sensor 290 such that it does not exceed the maximum force threshold. The maximum force threshold is continuously monitored by the controller 147 based on the feedback from the force sensor 292. This acts as a so-called "watchdog" function to ensure safe functionality of the system 2. Thus, if the maximum threshold is exceeded, the controller 147 terminates the operational sequence by cutting off supply of electrical current to the motor 152 and/or notifying the user of the error.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical system comprising:
   an adapter assembly including a first storage device;
   an end effector configured to couple to a distal portion of the adapter assembly, the end effector including a second storage device; and
   a surgical device configured to couple to a proximal portion of the adapter assembly, the surgical device including:
      a power source;
      a motor coupled to the power source, the motor configured to actuate at least one of the adapter assembly or the end effector;
      a memory; and
      a controller operatively coupled to the motor and configured to:
         calibrate the motor during a first calibration while the adapter assembly is actuated by the motor, without the end effector being coupled to the adapter assembly;
         measure a first parameter associated with actuation of the adapter assembly;
         calibrate the motor during a second calibration while the end effector is coupled to the adapter assembly and the end effector is actuated by the motor;
         measure a second parameter associated with actuation of the end effector;
         obtain calibration data during the first calibration and the second calibration based on the first parameter and second parameter;
         store calibration data in the memory in response to calibration of the motor; and
         update at least one of the first storage device or the second storage device based on the calibration data.

2. The surgical system according to claim 1, further comprising:
   a force sensor coupled to at least one of the adapter assembly, the end effector, or the motor, the force sensor configured to measure a force imparted on at least one of the adapter assembly, the end effector, or the motor.

3. The surgical system according to claim 2, wherein the force sensor is coupled to the controller and is configured to provide a force measurement signal indicative of the force.

4. The surgical system according to claim 3, wherein the calibration data is based on the force measurement signal.

5. The surgical system according to claim 4, wherein the controller is further configured to operate the motor based on the calibration data.

6. The surgical system according to claim 4, wherein the first storage device stores a first value corresponding to operation of the adapter assembly.

7. The surgical system according to claim 6, wherein the controller is further configured to read the first value and to adjust the first value based on the calibration data to obtain an adjusted first value.

8. The surgical system according to claim 7, wherein the controller is further configured to operate the motor based on the adjusted first value.

9. The surgical system according to claim 4, wherein the second storage device stores a second value corresponding to operation of the adapter assembly.

10. The surgical system according to claim 9, wherein the controller is further configured to read the second value and to adjust the second value based on the calibration data to obtain an adjusted second value.

11. The surgical system according to claim 10, wherein the controller is configured to operate the motor based on the adjusted second value.

12. A method for controlling a surgical system comprising:
    coupling an adapter assembly to a surgical device, the adapter assembly including a first storage device;
    energizing a motor of the surgical device during a first calibration to actuate at least one of the adapter assembly;
    measuring a first parameter associated with actuation of the adapter assembly;
    coupling an end effector to the adapter assembly, the end effector including a second storage device;
    energizing the motor of the surgical device during a second calibration to actuate the end effector;
    measuring a second parameter associated with actuation of the end effector;
    obtaining calibration data based on the first parameter and the second parameter;
    storing calibration data in a memory coupled to a controller; and
    updating at least one of the first storage device or the second storage device based on the calibration data.

13. The method according to claim 12, wherein the measurement of the first parameter and the second parameter is performed by a force sensor coupled to at least one of the adapter assembly, the end effector, or the motor.

14. The method according to claim 13, wherein measurement of the first parameter and the second parameter includes measuring a force imparted on at least one of the adapter assembly, the end effector, or the motor, the force sensor.

15. The method according to claim 14, further comprising transmitting a force measurement signal indicative of the force to the controller.

16. The method according to claim 15, further comprising:
    generating the calibration data based on the force measurement signal.

17. The method according to claim 16, further comprising operating the motor based on the calibration data.

18. The method according to claim 17, further comprising:

reading a value corresponding to operation of at least one of the end effector or the adapter assembly from a storage device associated with at least one of the end effector or the adapter assembly; and operating the motor based on the value adjusted by the calibration data.

\* \* \* \* \*